United States Patent [19]

Parsons, Jr.

[11] 4,292,296

[45] Sep. 29, 1981

[54] DIAGNOSTIC METHOD

[75] Inventor: George H. Parsons, Jr., Arlington, Mass.

[73] Assignee: Baxter Travenol Laboratories, Inc., Deerfield, Ill.

[21] Appl. No.: 941,707

[22] Filed: Sep. 12, 1978

[51] Int. Cl.$^3$ .................... G01N 33/48; A61K 43/00; G01T 1/00
[52] U.S. Cl. ................................ 424/1; 23/230 B; 424/12
[58] Field of Search ..................... 429/1, 12; 23/230 B

[56] References Cited

U.S. PATENT DOCUMENTS

| | | | |
|---|---|---|---|
| 3,799,740 | 3/1974 | Mincey | 23/230 B |
| 3,896,218 | 7/1975 | Charm et al. | 424/1 |
| 3,941,564 | 2/1976 | Fader et al. | 23/230 B |
| 3,960,492 | 6/1976 | Digiiulio | 424/1 |
| 3,980,764 | 9/1976 | Adams | 424/1 |
| 4,012,494 | 3/1977 | Ling | 424/1 |
| 4,016,250 | 4/1977 | Saxena | 424/1 |
| 4,032,626 | 6/1977 | Ward | 424/1 |
| 4,046,870 | 9/1977 | Hertl et al. | 424/1 |
| 4,052,504 | 10/1977 | Hertl et al. | 424/1 |
| 4,120,945 | 10/1978 | Gutcho et al. | 424/1 |
| 4,225,574 | 9/1980 | Romelli et al. | 424/1 |

FOREIGN PATENT DOCUMENTS 2731028  1/1979  Fed. Rep. of Germany .......... 424/1

OTHER PUBLICATIONS

Ellis et al., Symposium on Radioimmunoassay and Related Topics in Biochem. M187194 (1972).
Kumagai et al., Abstracts of Papers Submitted to the 20th Ann. Meeting of the Western Society for Clinical Research p. 124 (1967).
Damon Diagnostics, "LiquiSol" TM Issued 9/1/78.
Lee et al., J. Clin. Endocrin. Metab., 24:486 et seq. (1964).
Cvaron et al., Acta Endocrinologica, 46 (2) 161-169 (1964).
Oppenheimer et al., J. Clin. Invest, 42 (11) 1769 et seq. (1963).
Chemical Abstracts, 67: 98546p, (1967).
Chemical Abstracts, 81: 116799u (1974).
Chemical Abstracts, 83: 39736 (1975).
Chemical Abstracts, 86: 13354u (1977).
Chemical Abstracts, 87: 163779w (1977).
Chemical Abstracts, 79: 143962g (1973).
Odstrchel et al., International Symposium on Radioimmunoassay and Related Procedures in Medicine, pp. 1-5, W. Berlin 31 Oct-4 Nov. 1977.
Cavalieri et al., J. Null. Med., vol. 10, No. 9, 1969, pp. 565-570.

Primary Examiner—Deborah L. Kyle
Assistant Examiner—Christine M. Nucker
Attorney, Agent, or Firm—Paul C. Flattery; Lawrence W. Flynn; Max D. Hensley

[57] ABSTRACT

Free analytes in samples containing free analytes and receptorbound analytes are determined by absorbing at least a portion of free analyte from the sample with insolubilized receptor or receptor which is then made insoluble, washing the insoluble receptor, adding labelled sample analyte or labelled sample analyte receptor, incubating, washing the insoluble phase free of the soluble phase and determining the label in either phase. The method solves a long standing need in the assay of free thyroid hormones.

41 Claims, No Drawings

DIAGNOSTIC METHOD

BACKGROUND OF THE INVENTION

This invention relates to the assay of free analytes. For the purposes of this invention the unbound free analyte shall be taken as a substance present in a sample in which a proportion of the substance is unbound and a proportion is bound to a receptor. Generally a predominant proportion of the substance will be reversibly, albeit firmly bound to the receptor. Also, in many instances the receptor will have sites available for binding additional analyte even though, according to the Law of Mass Action, there will be a very small amount of analyte free in solution. The receptor will ordinarily be soluble, and in most cases is a protein.

The importance of free analytes is that the physiological action of many drugs and hormones correlates much more closely with the concentration of free drugs or hormones in circulation than with their total levels. Examples of such free analytes and their receptors are thyroid hormones with thyroxine binding proteins (TBP); aldosterone, progesterone and testosterone with sex hormone binding globulin; diphenylhydantoin with albumin; antihemophilic factor with its inhibitors; proteolytic enzymes with their inhibitors or activators; cortisol with cortisol binding protein; and vitamin $B_{12}$ with intrinsic factor. Many others are known or will become known in the future. The most thoroughly investigated and the most important of these systems is the thyroid hormone-TBP binding system. Since most of the prior art relates to this system, free thyroid assays are largely the subject of the following discussion. However, it should be noted that the same problems and methods will be relevant to the determination of other free analytes.

Functional thyrometabolic status has been commonly evaluated by measurement of the total serum content of the thyroid hormone thyroxine (3,5,3′,5′-L-tetraiodothyronine, T4). Greater than 99.95% of the circulating T4 serves as a metabolically inert reservoir transported in serum bound primarily to thyroxine binding globulin (TBG), and secondarily to thyroxine binding prealbumin (TBPA) and albumin, collectively termed thyroxine binding protein (TBP). A great deal of evidence exists that the remaining less than 0.1% of the free or unbound fraction of circulating T4 is physiologically active because it diffuses into tissue to exert its action, its concentration is an important determinant of the hormone removal rate, and anomalies in TBP do not normally affect its concentration. It is thought to be the precursor of triiodothyronine (T3), which is also present in serum in the free and protein-bound forms. Again, the free T3 level correlates best with functional thyroid status.

The absolute quantity of T4 in samples, regardless of its free or bound status, has been measured by total T4 tests. The usual procedure involves denaturing TBP with alcohol or adding a displacing agent such as salicylate to release a large proportion of the T4 into solution, followed by addition of radioisotope labelled T4 and a T4 receptor such as an ion exchange resin or insoluble antibody. Sample and labelled T4 are allowed to compete for limited sites on the receptor, then the receptor is separated from the soluble reactants and the amount of radioactivity bound to the receptor is determined. This radioactivity is inversely proportional to the amount of sample T4 originally present. However, since total T4 rises and falls with the TBP, particularly TBG, levels in the euthyroid individual, an abnormal thyroid function may be erroneously indicated by any factor which changes the concentration of the binding proteins. Androgens, estrogens, anabolic steroids, glucocorticoids, and normal pregnancy alter the TBG levels. Thus the total T4 assay alone has not been found to be a reliable indicator of the thyrometabolic status.

Alterations in TBG levels are usually compensated for by a shift in the total T4 levels, as the negative feedback mechanism of the hypothalamic-thyroid axis works to keep the free T4 concentration constant. The unbound or "free" portion of thyroxine in serum is therefore the most useful constant indicator of thyrometabolic status. The amount of unbound thyroxine is governed by the Law of Mass Action, and is largely a function of the total circulating T4 and the concentration of TBG.

The difficulties of correlating thyrometabolic status with total T4 led to the development of the thyroid hormone uptake assay. This test measures the relative amount of serum TBP binding capacity, i.e., that which has not already been occupied by uptake of thyroid hormone in vivo. Thyroid hormone uptake immunoassays are ordinarily conducted by adding labelled T3 to a serum sample until the T3 is absorbed by the unsaturated TBP binding sites, scavenging the unabsorbed T3 from the reaction mixture by contacting the mixture with an insoluble T3 receptor such as an ion exchange resin or antibody and measuring the scavenged labelled T3. T4 may also be used. A proportionately large number of unoccupied binding sites will be indicated by a commensurately low amount of labelled thyroid hormone bound to the insoluble receptor.

In lieu of a direct free T4 measurement the percentage thyroid hormone uptake has been multiplied times the results of a total T4 or protein bound iodine assay on the same sample to arrive at the Free Thyroxine Index (Clark et al., "Journal Clin. Endocrinol." 25:39–45 [1965]). The Free Thyroxine Index is based on the premise that the uptake result is inversely proportional to the unsaturated TBP in serum and that free T4 varies directly with total T4 and inversely with unestimated TBP levels. The Free Thyroxine Index suffers from various disadvantages. It is capable of limited sensitivity and precision, separate determinations are required, and the uptake test upon which the Index is based may give erroneous values when used on sick euthyroid patients, persons with hereditary TBG deficiency, persons with increased TBP concentrations, and in those patients undergoing therapy with drugs such as phenylbutazone, diphenylhydantoin, salicylate and prednisone.

A requirement for two separate determinations is also an integral part of the kinetic free T4 assay disclosed in U.S. Pat. No. 4,046,876. Here two series of tubes are assayed. In both series an equilibrium is first established between labelled T4, endogenous sample T4 and TBP. In one series an agent is present to displace a large proportion of the T4 from TBP, i.e., this series produces a determination of total T4. Since the other series contains no such agent it will essentially yield a T4 uptake determination. Then each reaction mixture is added to insoluble T4 antibody, incubated for a set period, the phases separated and the solid phase assayed for the label. The relative reaction rates in the two series are calculated for each pair of tubes and the results compared with a standard plot. Aside from the disadvantages of requiring two sets of assays for each determination, as with the closely related Free Thyroxine Index, this method requires tedious calculations. Also, since it is a kinetic method it is highly time dependent, thus making it difficult to accurately conduct large numbers of determinations simultaneously.

U.S. Pat. No. 3,799,740 discloses a technique for obtaining in a single container a measure of free T4, the Effective Thyroxine Ratio. However, the method is still essentially based upon a dual assessment of thyroid hormone uptake and total T4. In accordance with this method sample T4 is extracted from TBG and an aliquot of this extract is combined with a complex of labelled T4 with TBG and with an aliquot of unsaturated TBG from the same sample. An anion-selective resin is then added to the reaction mixture, incubated for a carefully controlled period, the resin removed and the amount of label in the supernatant determined. While a portion of the analytical steps of this method may be performed in a single container the T4 extraction procedure is burdensome and introduces considerable error into the determination. Other error is introduced during the handling of two sample aliquots. Finally, the method is overall procedurally complex.

Similarly, U.S. Pat. No. 3,941,504 discloses a free T4 assay which may be conducted within a single container. Here a sample and an aliquot of labelled T4 are combined, then the labelled and unlabelled T4 are extracted from the serum TBP on a dextran gel column at high pH. A percentage of the total added label is retained by the column upon elution with unsaturated TBP and a portion of the pre-extracted sample. This percentage, the Free Thyroxine Equivalent, is an indirect measure of free T4 which may be quantitated by comparison with appropriate standards. While this method does not expressly call for a total T4 assay as part of the procedure it nonetheless suffers from the same errors introduced during the extraction of T4 and labelled T4 from TBG on the dextran gel column. Further, column chromatography is inconvenient, imprecise and not suited to large scale clinical use. This method also entails handling duplicate patient samples, a ready source for error, and includes an undue number of manipulative steps.

Another group of related assays, generically termed the free thyroxine tests, also requires determination of the total endogenous T4. In these tests serum isincubated with labelled T4 until labelled and unlabelled T4 are uniformly distributed between TBP and the free proportion of T4. Simultaneously with or following this incubation the unbound T4 is separated from the TBP-bound fraction using a variety of techniques, e.g., charcoal or dextran gel absorption, ultrafiltration or dialysis. Again, the result is mathematically combined with the results of a total T4 determination on the same sample. These tests therefore suffer from the principal defect noted for other free T4 methods, i.e., the need for a total T4 assay to quantitate the percentage free T4 yielded by the other member of the dual assay. This multiplies the errors involved in each test and doubles the expense and time required. Some special problems are also encountered with these methods, e.g., the need for highly purified labelled T4 in the dialysis and ultrafiltration techniques. Examples of these methods are Oppenheimer et al, "Journal of Clinical Investigation" 42(11):1769–1782 (1963) and Cavalieri et al, "Journal of Nuclear Medicine" 10(9):566–570 (1969). A similar assay for free testosterone using dialysis separation is known.

Finally, free T4 has been directly determined by dialyzing a sample and assaying the dialysate by gas chromatography or electrophoresis. These methods lack the sensitivity, precision and simplicity of binding assays, require a great deal of technical skill and are too slow for routine laboratory use.

OBJECTS OF THE INVENTION

Accordingly, a general object of this invention is to reduce the technical and theoretical disadvantages of known free analyte assays as well as the time and skill required to conduct such assays.

It is another object of this invention to improve the precision of known free analyte assays, to lower their cost and to reduce the number of reagents required by such assays.

It is a principal object of this invention to dispense with the need for a total analyte assay in determining free analyte concentration.

It is an object of this invention to provide a method for the direct determination of free analyte.

An additional object of this invention is to eliminate sample analyte extractions in assays for free analyte concentration.

A further object of this invention is to eliminate handling of duplicate aliquots of samples to be determined.

Another object of this invention is to simplify the removal of free analyte from solutions containing endogenously bound analyte.

These and other objects will be apparent from consideration of the invention as a whole.

SUMMARY OF THE INVENTION

The above objects are achieved by performing the free analyte determination in essentially two steps. In the first step the native sample is contacted with an absorbent for the analyte to remove free analyte from solution. In the second step the absorbent-bound analyte is contacted with labelled analyte analogue or labelled receptor for the analyte. Then, as in the prior assays, the soluble phase is removed from the absorbent and the amount of label in either is determined. However, it is entirely unnecessary to then determine the total analyte, unlike in the previously known methods for free analyte, because the inventive method is a direct, quantitative measure of free analyte rather than a percentage. The results may be simply plotted on a typical standard curve and the free analyte directly determined. This invention remarkably lifts the burdens of the previously known techniques for free analytes and substitutes an elegant, sensitive, precise and straightforward procedure.

The disclosed method for directly determining free analyte concentration comprises (a) contacting the sample with an unlabelled receptor for the analyte to bind said free analyte, (b) removing the sample from contact with the receptor; (c) contacting the receptor with a labelled reagent selected from the group of a labelled analyte analogue or a labelled, soluble analyte receptor; (d) separating the receptor from unbound labelled reagent; and (e) measuring the amount of bound or unbound label.

DESCRIPTION OF THE PREFERRED EMBODIMENTS

The method of this invention is applicable to any free analyte. Most such analytes will be relatively low molecular weight compounds, generally on the order of up to about 3000 molecular weight. The predominate classes of free analytes will be drugs and hormones. Exemplary drugs are cortisol and diphenylhydantoin while particular hormones of interest are progesterone, insulin and the thyroid hormones, particularly T4.

There are at least three analyte receptors involved in the method of this invention. The sample receptor is the native receptor found in the sample as a complex with various amounts of analyte. The labelled and unlabelled receptors are both reagents employed in the method. While the unlabelled receptor is used to bind free analyte in all embodiments of this invention, the labelled receptor is only employed in one specific alternative. Two or more of these receptors may be the same or they may be all different.

The unlabelled receptor for analyte must be carefully chosen. As a general proposition it should have a very high affinity for the analyte but a low capacity for binding the analyte, i.e., it should not be capable of absorbing significantly larger quantities of analyte than are expected to be found free in the sample. This is because the step of contacting unlabelled receptor with the sample is directed towards binding the normally free analyte. It is not preferred that analyte be stripped from the analyte-receptor complex in the sample. Otherwise, the assay sensitivity may be adversely affected and if a large enouth proportion of the analyte is absorbed from the analyte-receptor complex, the procedure will essentially measure total analyte concentration. Further, if the capacity and affinity of the unlabelled receptor differs radically from that of the sample analyte receptor a degree of time dependency in the first step absorption will be introduced into the assay, caused by the gradual removal of analyte from its complex with sample receptor. In most instances this removal will not result in artificially high levels of free analyte because a parallel absorption will occur in the standards and controls, but the incubation time of standards, controls and samples should be closely controlled.

Suitable unlabelled receptors are weak ion exchange resins, inorganic sorbent materials such as disclosed in U.S. Pat. No. 3,666,854, or proteins such as analyte antibody. Where the unlabelled analyte receptor is insolubilized prior to contact with the sample the same analyte receptor as is found in the sample analyte-receptor complex may be used, for example TBG. However, analyte antibody is preferred, and for free thyroxine assay a calculated affinity constant of about $1.4 \times 10^{10}$ liters/mole has been found to be satisfactory.

The unlabelled receptor is ordinarily insolubilized to facilitate removal of the sample from contact with the receptor. Before, during or after free analyte binding the receptor may be insolubilized by absorbing or covalently bonding it to an inert surface, or by aggregating or covalently crosslinking the receptor until it becomes insoluble, e.g., by polyethylene glycol precipitation or glutaraldehyde crosslinking in accordance with known techniques. Also known are methods for absorbing or bonding receptors such as proteins to insoluble supports. One particularly preferred conventional technique is the absorption of an analyte antibody onto the inner wall of plastic test tubes prior to contact with the sample. Here the test tube becomes the sole reaction container for the entire free analyte determination, and manipulation of reagents is considerably simplified because centrifugation or filtration are not needed to separate soluble from insoluble phases in performing the method. Although it is within the scope of this invention to insolubilize the unlabelled receptor after it has bound the free analyte it is clearly necessary that the insolubilization technique in such cases not also render the sample receptor insoluble. Where the sample and unlabelled receptor are immunologically distinct the unlabelled receptor may be precipitated after absorption of free analyte and in the presence of sample receptor by simply adding sufficient unlabelled-receptor antibody to effect an immune precipitation of unlabelled receptor.

The amount of unlabelled receptor used will be a function of its capacity and affinity for analyte under the conditions of the assay. However, the amount expressed as binding sites alone is usually greater than the estimated range of free analyte to be found in the sample but less than the total of the labelled reagent and estimated free analyte. Where the labelled reagent is labelled analyte analogue the unlabelled receptor binding sites must be limiting. Conventional antibody-absorbed test tubes previously employed in total analyte determinations, e.g., total T4, are satisfactory.

The labelled analyte receptor must be soluble, and it is only practical to use such a receptor where the analyte can simultaneously bind two receptors, i.e., unlabelled and labelled analyte receptor. For example, where both the unlabelled and labelled receptors are analyte antibodies the analyte must be polyepitopic. As a consequence, labelled receptors are ordinarily used for high molecular weight analytes, which are more likely to have at least two binding sites. Labelled receptors and methods for making them are well known, such receptors having been used for some time in sandwich immunoassays and histochemistry. Since maximum binding of labelled receptor to analyte is desired when using this particular labelled reagent, it is preferred that the receptor be chosen for as high an affinity and capacity as is possible so as to bind to a maximum of analyte. It is preferred to use analyte antibody which has been radioisotopically labelled.

The labelled analyte analogues are also a well-known class of reagents. They are made by replacing at least one atom of the native analyte with a detectable group, ordinarily a radioisotope or enzyme, which may be linked to the analyte by a carrier group or by direct substitution of an analyte atom. An example of the latter is T4 in which one of the iodine atoms has been replaced with a radioisotope of iodine such as $^{125}$I or $^{131}$I.

Suitable labels are known for the labelled reagent, whether the analyte analogue or analyte receptor. For example, in addition to enzymes and radioisotopes it is within the scope of this invention to use stable free radicals, fluorescent compounds or reactants such as coenzymes or chemiluminescent compounds.

In the method of this invention a sample containing free analyte and receptor-bound analyte is contacted with unlabelled analyte receptor. As described above the unlabelled receptor is preferably analyte antibody absorbed onto the inner surface of a plastic container, for example a polypropylene test tube. If the receptor is a protein it may be crosslinked with glutaraldehyde and absorbed to the surface in accordance with U.S. Pat. No. 4,069,352.

It generally is not advantageous to use full strength sample, particularly where the sample is blood serum. The elevated solute concentration of such samples may adversely affect the performance of the analyte receptor. Further, antibody-coated surfaces are relatively low capacity, high affinity receptors. Their effective use with the extremely low concentrations of free analyte frequently found in samples is considerably aided by sample dilution. Sample dilution displaces a small amount of analyte from its receptor which, when combined with free analyte, results in sufficient analyte being bound to the surface to conduct subsequent receptor-bound analyte determination. Thus it is preferred to add water or a buffer to the sample in about from 2 to 15 times the sample volume, either before or during contact of the sample with the unlabelled receptor. Ordinarily a 1:11 dilution of sample into 0.01 M phsophate buffered saline containing a small amount of bovine serum albumin is acceptable.

The reaction mixture, which contains no labelled reagent, is incubated for a period and at a temperature sufficient for the receptor to absorb at least a significant portion of the free analyte. These parameters will range widely depending upon such factors as ionic strength, sample dilution, and receptor affinity. Since the equilibrium in favor of analyte association with receptor is considerably greater than that of dissociation from the endogenous analyte-receptor complex it is preferred to use only a brief incubation at this point, e.g., about from 5 to 30 minutes, and a temperature at which the reaction components are stable. A preferred incubation for a free T4 determination is about 10 minutes at about 37° C. using the above described sample dilution and T4 antibody affinity.

After the incubation the unlabelled receptor-bound analyte is separated from the other reaction components. This may be accomplished by the receptor insolubilization techniques described above. However, aspirating or decanting the liquid contents of a receptor-coated tube is most convenient. A buffer or water wash of the insoluble receptor-bound analyte is preferred to ensure that the insoluble material is substantially free of sample receptor or sample receptor-bound analyte.

Next the amount of bound analyte is assayed by addition of either labelled analyte analogue or labelled soluble analyte receptor, followed by separation of the soluble from insoluble phases and determination of the label content of at least one of the phases. Preferably a labelled analyte analogue is used, in which case the insoluble receptor binding sites must be less than about the total of analyte and labelled analyte so that a competitive displacement equilibrium can take place. Otherwise, the amount of receptor binding sites are generally irrelevant unless non-specific labelled receptor binding becomes a problem. The quantity of labelled analyte analogue is not critical. The quantity of labelled receptor should be greater than the amount of unlabelled receptor-bound analyte. The labelled reagents are ordinarily added as buffered solutions.

Ordinarily the labelled reagent will be permitted to equilibrate with the insoluble receptor-bound analyte before the phase separation. It is possible to increase the assay sensitivity by removing the labelled reagent before a significant amount of receptor-bound analyte has dissociated into solution. However, whatever dissociation does occur is time dependent and accordingly it is difficult to conduct assays on large groups of samples. It is preferable instead to allow the reaction mixture to reach a steady state. Equilibrium is dependent upon the same factors as analyte binding by unlabelled receptor and may be readily determined by the skilled artisan. In the case of T4, an about 1 hour incubation at about 37° C. is satisfactory.

The phase separation is effectively accomplished by known techniques such as centrifugation, filtration or, when using coated tubes, decantation or aspiration. The insoluble product may then be washed with water or buffer as in the preceding steps. Preferably the insoluble material is then assayed for its label content, although the residual soluble labelled reagent may also be determined. The results with samples are then compared with similarly treated controls and standards by interpolation to arrive at a direct, quantitative measure of free analyte.

The invention will be more fully understood by reference to the following examples.

EXAMPLE 1

This example demonstrates the ease with which an assay of free T4 in two patient samples may be conducted using the inventive method. Polypropylene tubes coated with rabbit antibody to T4 were marked in duplicate according to the following scheme.

TABLE 1

| Tube No. | Contents of Tubes | Free T4 Added (pg in 0.1 ml) |
|---|---|---|
| 1,2 | Free T4 Serum Blank, 0 ng/dl | 0 |
| 3,4 | Free T4 Serum Standard, 0.25 ng/dl | 0.25 |
| 5,6 | Free T4 Serum Standard, 1.0 ng/dl | 1.00 |
| 7,8 | Free T4 Serum Standard, 2.9 ng/dl | 2.90 |
| 9,10 | Free T4 Serum Standard, 4.9 ng/dl | 4.90 |
| 11,12 | Free T4 Serum Standard, 7.35 ng/dl | 7.35 |
| 13,14 | Patient "X" Serum Sample | "x" |
| 15,16 | Patient "Y" Serum Sample | "y" |

Duplicate samples were used for statistical reasons, not because of a mandatory assay requirement. The following reagents were allowed to reach ambient temperature and added to the appropriate tubes in duplicate;

(a) 100 microliters of free T4 Serum Blank, 0 ng/dl;

(b) 100 microliters of each free T4 Serum Standards in concentrations of 0.25, 1.0, 2.9, 4.9 and 7.35 ng/dl; and (c) 100 microliters of each sample.

Care should be taken that the pipetting of the 100 microliter aliquots is done reproducibly, and in the same manner for both standards and samples. 1.0 ml of pH 7.4 0.01 M phosphate buffered saline containing bovine serum albumin and warmed to 37° C. was added to each tube to dilute the samples, standards and blank. The samples and buffer were mixed by vortexing. All tubes were then incubated in a 37° C. water bath for 10 minutes, after which the contents of the tubes were aspirated. 1.0 ml of $^{125}I$ T4 in tris buffer (0.5 uCi) pH 8.5 containing 0.006 M sodium salicylate, 0.004 M 8-anilino-1-napthaline-sulfonic acid and 0.7 M sodium chloride was added and the tubes incubated for 60 minutes at 37° C. The contents of all tubes were aspirated and the radioactivity of the tubes then counted in a gamma counter for one minute with the window adjusted for iodine-125. The results of this assay are set forth in Table 2 below. The counts per minute for the standards were then plotted on semilogarithmic graph paper and the free T4 concentration in the patient serum unknown samples determined by interpolation. The patient serum results are also set forth in Table 2.

TABLE 2

| Tube No. | Contents of Tubes | Counts per Minute (bound) | Free T4 Concentration (ng/dl) |
|---|---|---|---|
| 1 | Free T4 Serum Blank | 26,458 | 0 |
| 2 | " | 26,269 | 0 |
| 3 | Free T4 Standard | 25,054 | 0.25 |
| 4 | " | 24,487 | 0.25 |
| 5 | Free T4 Standard | 21,044 | 1.0 |
| 6 | " | 21,090 | 1.0 |
| 7 | Free T4 Standard | 16,412 | 2.9 |
| 8 | " | 16,737 | 2.9 |
| 9 | Free T4 Standard | 14,442 | 4.9 |
| 10 | " | 14,991 | 4.9 |
| 11 | Free T4 Standard | 13,012 | 7.35 |
| 12 | " | 13,447 | 7.35 |
| 13 | Patient "X" Serum Sample | 20,356 | 1.25 |
| 14 | " | 20,664 | 1.15 |
| 15 | Patient "Y" Serum Sample | 18,054 | 2.2 |
| 16 | " | 17,281 | 2.5 |

EXAMPLE 2

A series of serum samples from pregnant women were assayed for percent T3 uptake, total T4 and by the method described in Example 1. The Free Thyroxine Index (FTI) was calculated from the results with the first two assays and compared with the Example 1 method. As can be seen from Table 3 below, the results achieved by the method of this invention correlate well with those of the heretofore employed Free Thyroxine Index.

TABLE 3

| Specimen | % T3U (30–40%) | Total T4 (4.5–11.5 ug%) | FTI (4.5–11.5 ug%) | Free T4 (0.8–2.3 ng/dl) |
|---|---|---|---|---|
| 265 | 25.3 | 15.4 ug% | 11.11 ug% | 2.3 ng/dl |
| 272 | 25.6 | 14.1 | 10.34 | 1.8 |
| 271 | 27.3 | 11.8 | 9.19 | 1.4 |
| 274 | 24.9 | 11.6 | 8.27 | 1.2 |
| 295 | 31.6 | 11.5 | 10.42 | 1.8 |
| 308 | 25.8 | 8.6 | 6.32 | 1.4 |
| 310 | 23.6 | 18.2 | 12.27 | 1.5 |
| 311 | 30.5 | 8.6 | 7.51 | 1.8 |
| 313 | 23.6 | 12.4 | 8.36 | 1.9 |
| 345 | 23.7 | 11.2 | 7.59 | 1.0 |
| 368 | 24.4 | 12.1 | 8.45 | 1.3 |

The above examples and other specific information contained herein are for purposes of illustration only. Such alterations and modifications thereof as would be apparent to those skilled in the art are deemed to fall within the scope and spirit of the invention bearing in mind that the invention is defined only by the appended claims.

What is claimed is:

1. A method for directly determining free, unbound analyte in a sample containing a proportion of analyte bound to a receptor in the sample, comprising
   (a) contacting the sample with an unlabelled receptor for the analyte to bind the free analyte in the sample;
   (b) removing the sample from contact with the unlabelled receptor;
   (c) contacting the unlabelled receptor with a labelled reagent selected from the group of
      (i) a labelled analyte analogue, or
      (ii) a labelled, soluble analyte receptor;
   (d) separating the receptor of step c from unbound labelled reagent;
   (e) measuring the amount of bound or unbound label; and
   (f) correlating the measured amount in step (e) with the amount of free analyte in the sample.

2. The method of claim 1 wherein the label is a radioisotope.

3. The method of claim 1 wherein said analyte receptor is an antibody.

4. The method of claim 3 wherein the antibody is coated onto at least a portion of the inner surface of a container.

5. The method of claim 1 wherein at least substantially all of the free sample analyte is absorbed from the sample.

6. The method of claim 1 wherein the unlabelled analyte receptor is washed after it is contacted with sample analyte but before it is contacted with labelled reagent.

7. The method of claim 1 wherein the sample analyte is a drug.

8. The method of claim 4 wherein the sample is diluted before or during contact with the unlabelled receptor.

9. The method of claim 1 wherein the sample analyte is thyroxine, triiodothyronine, testosterone or diphenylhydantion.

10. The method of claim 1 wherein the labelled reagent is labelled analyte analogue.

11. The method of claim 10 wherein the quantity of receptor is such that the number of its binding sites is less than the combined amount of sample analyte and sample analyte analogue.

12. The method of claim 11 wherein said receptor is contacted with the labelled analyte analogue until the sample analyte analogue and sample analyte associate with and dissociate from the receptor, respectively, to a point of stable equilibrium.

13. The method of claim 1 wherein said labelled reagent is labelled analyte receptor.

14. The method of claim 13 wherein the quantity of receptor is such that the number of its binding sites is at least equal to the amount of sample analyte.

15. A method for determining free thyroid hormone in a fluid also containing endogenously bound thyroid hormone, comprising:
   (a) contacting said fluid with a receptor for said hormone whereby free hormone is absorbed from the fluid;
   (b) separating the receptor from the fluid;
   (c) contacting the receptor with labelled hormone;
   (d) separating the receptor from unbound, labelled hormone;
   (e) determining the amount of unbound or receptor-bound labelled hormone; and
   (f) correlating the measured amount in step e with the amount of free hormone in the fluid.

16. The method of claim 15 wherein the thyroid hormone is thyroxine.

17. The method of claim 15 wherein the receptor is a thyroxine antibody coated onto at least a portion of the inner surface of a container and the fluid is a diluted sample.

18. The method of claim 16 wherein at least substantially all of the free thyroxine is absorbed from the fluid.

19. The method of claim 16 wherein the fluid is blood serum diluted about from 1 to 15 times.

20. The method of claim 16 wherein the receptor is contacted with labelled hormone until free receptor binding sites are occupied with labelled hormone but before essentially any dissociation of sample hormone from the receptor.

21. The method of claim 20 wherein the receptor is contacted with labelled hormone until the receptor reaches equilibrium with the labelled and sample thyroid hormone.

22. The method of claim 15 wherein the receptor is washed after it is separated from the fluid.

23. The method of claim 17 wherein the thyroxine antibody is reacted with glutaraldehyde before the thyroxine antibody is coated onto the surface.

24. The method of claim 15 wherein the amount of receptor-bound labelled hormone is determined.

25. The method of claim 15 wherein the label is a radioisotope.

26. The method of claim 25 wherein the radioisotope is radioiodine.

27. The method of claim 15 wherein the fluid is undiluted blood serum and a diluent is added to the serum before separating the receptor from the serum.

28. The method of claim 27 wherein a sufficient amount of diluent is added to dilute the serum about from 1 to 15 times.

29. A method for directly determining free unbound analyte in a sample containing a proportion of analyte bound to a receptor in the sample, comprising
(a) contacting the sample with an unlabelled receptor for the analyte to bind the free analyte in the sample, the affinity and capacity of the unlabelled receptor being selected so that the receptor will not adsorb analyte bound to sample receptor;
(b) removing the sample from contact with the unlabelled receptor;
(c) contacting the unlabelled receptor with a labelled reagent selected from the group of
(i) a labelled analyte analogue, or
(ii) a labelled, soluble analyte receptor;
(d) separating the receptor of step (c) from unbound labelled reagent;
(e) measuring the amount of receptor-bound or unbound label; and
(f) correlating the measured amount in step (e) with the amount of free analyte in the sample.

30. A method for directly determining free, unbound analyte in a sample containing a proportion of analyte bound to a receptor in the sample, wherein the analyte has a molecular weight up to about 3000, comprising
(a) contacting the sample with an analyte antibody adsorbed to the inner surface of a container;
(b) removing the sample from contact with the analyte antibody;
(c) contacting the antibody with a labelled analyte analogue;
(d) separating the antibody from unbound labelled analyte analogue;
(e) measuring the amount of antibody-bound or unbound label; and
(f) correlating the measured amount in step (e) with the amount of free analyte in the sample.

31. A method of directly determining free, unbound aldosterone in a sample containing a proportion of aldosterone bound to sex hormone binding globulin in the sample, comprising
(a) contacting the sample with a aldosterone antibody adsorbed to the inner surface of a container;
(b) removing the sample from contact with the aldosterone antibody;
(c) contacting the antibody with labelled aldosterone;
(d) separating the antibody from unbound labelled aldosterone;
(e) measuring the amount of antibody-bound or unbound label; and
(f) correlating the measured amount in step (e) with the amount of free aldosterone in the sample.

32. A method for directly determining free, unbound progesterone in a sample containing a proportion of progesterone bound to sex hormone binding globulin in the sample, comprising
(a) contacting the sample with a progesterone antibody adsorbed to the inner surface of a container;
(b) removing the sample from contact with the progesterone antibody;
(c) contacting the antibody with labelled progesterone;
(d) separating the antibody from unbound labelled progesterone;
(e) measuring the amount of antibody-bound or unbound label; and
(f) correlating the measured amount in step (e) with the amount of free progesterone in the sample.

33. A method for directly determining free, unbound testosterone in a sample containing a proportion of testosterone bound to sex hormone binding globulin in the sample, comprising
(a) contacting the sample with a testosterone antibody adsorbed to the inner surface of a container;
(b) removing the sample from contact with the testosterone antibody;
(c) contacting the antibody with labelled testosterone;
(d) separating the antibody from unbound labelled testosterone;
(e) measuring the amount of antibody-bound or unbound label; and
(f) correlating the measured amount in step (e) with the amount of free testosterone in the sample.

34. A method for directly determining free, unbound diphenylhydantoin in a sample containing a proportion of diphenylhydantoin bound to albumin in the sample, comprising
(a) contacting the sample with a diphenylhydantoin antibody adsorbed to the inner surface of a container;
(b) removing the sample from contact with the diphenylhydantoin antibody;
(c) contacting the antibody with labelled diphenylhydantoin;
(d) separating the antibody from unbound labelled diphenylhydantoin;
(e) measuring the amount of antibody-bound or unbound label; and
(f) correlating the measured amount in step (e) with the amount of free diphenylhydantoin in the sample.

35. A method for directly determining free, unbound cortisol in a sample containing a proportion of cortisol bound to cortisol binding protein in the sample, comprising
(a) contacting the sample with a cortisol antibody adsorbed to the inner surface of a container;
(b) removing the sample from contact with the cortisol antibody;
(c) contacting the antibody with labelled cortisol;
(d) separating the antibody from unbound labelled cortisol;

(e) measuring the amount of antibody-bound or unbound label; and
(f) correlating the measured amount in step (e) with the amount of free cortisol in the sample.

36. A method for directly determining free, unbound insulin in a sample containing a proportion of insulin bound to insulin antibody in the sample, comprising
   (a) contacting the sample with an insulin antibody adsorbed to the inner surface of a container;
   (b) removing the sample from contact with the insulin antibody;
   (c) contacting the antibody with labelled insulin antibody;
   (d) separating the container-absorbed antibody from unbound labelled insulin antibody;
   (e) measuring the amount of antibody-bound or unbound label; and
   (f) correlating the measured amount in step (e) with the amount of free insulin in the sample.

37. A method for directly determining free, unbound analyte in a native or diluted native sample containing a proportion of the analyte bound to a receptor in the sample, comprising
   (a) contacting the sample with an unlabelled receptor for the analyte to bind free analyte present in the sample;
   (b) removing the sample from contact with the unlabelled receptor;
   (c) then contacting the unlabelled receptor with a labelled analyte analogue;
   (d) separating the receptor of step c from unbound labelled analyte analogue;
   (e) measuring the amount of bound or unbound label; and
   (f) correlating the measured amount in step e with the amount of free analyte in the sample.

38. A method for directly determining free, unbound analyte in a sample containing a proportion of the analyte bound to a receptor in the sample, comprising
   (a) contacting the sample with an unlabelled receptor for the analyte to bind free analyte present in the sample;
   (b) washing the unlabelled receptor until it is substantially free of sample receptor or sample receptor-bound analyte;
   (c) then contacting the washed unlabelled receptor with a labelled analyte analogue;
   (d) separating the receptor of step c from unbound labelled analyte analogue;
   (e) measuring the amount of bound or unbound label; and
   (f) correlating the measured amount in step e with the amount of free analyte in the sample.

39. The method of claims 1, 29 or 38 wherein the sample is diluted before contact with unlabelled receptor for the analyte.

40. The method of claims 1, 29, 30, 37 or 38 wherein the analyte is a hormone.

41. The method of claims 1, 30, 37 or 38 in which at least a significant portion of the free analyte is bound by the unlabelled receptor.

* * * * *

UNITED STATES PATENT AND TRADEMARK OFFICE
CERTIFICATE OF CORRECTION

PATENT NO. : 4,292,296
DATED : September 29, 1981
INVENTOR(S) : George H. Parsons, Jr.

It is certified that error appears in the above-identified patent and that said Letters Patent are hereby corrected as shown below:

Column 3, line 47, of the last paragraph, insert a space between "is" and "in-".

Column 5, line 27, of the third paragraph "enouth" should read "enough".

Column 7, line 12, of the first paragraph "phsophate" should read "phosphate".

Column 9, Table 3, line 10, figure "1.5" should be "2.5".

Column 10, lines 5, 7, and 19 "claim" should read "claims 29, 30, 37, 38 or 1".

Signed and Sealed this

Tenth Day of August 1982

[SEAL]

Attest:

GERALD J. MOSSINGHOFF

Attesting Officer

Commissioner of Patents and Trademarks